United States Patent [19]

Lee

[11] Patent Number: 4,900,300
[45] Date of Patent: Feb. 13, 1990

[54] SURGICAL INSTRUMENT

[76] Inventor: David A. Lee, 2868 Nicada Dr., #48, Los Angeles, Calif. 90077

[21] Appl. No.: 315,190

[22] Filed: Feb. 24, 1989

Related U.S. Application Data

[63] Continuation of Ser. No. 70,325, Jul. 6, 1987, abandoned.

[51] Int. Cl.$^4$ .............................................. A61B 17/20
[52] U.S. Cl. .................................... 604/22; 606/162; 606/166
[58] Field of Search ........................... 604/22, 27, 28; 128/304, 305, 321, 757–758

[56] References Cited

U.S. PATENT DOCUMENTS

| | | | |
|---|---|---|---|
| 3,542,031 | 11/1970 | Taylor | 128/304 |
| 4,011,869 | 3/1977 | Seiler, Jr. | 604/22 |
| 4,043,322 | 8/1977 | Robinson | 604/22 |
| 4,210,146 | 7/1980 | Banko | 128/305 |
| 4,220,155 | 9/1980 | Kimberling et al. | 128/305 |
| 4,577,629 | 3/1986 | Martinez | 604/22 |
| 4,655,743 | 4/1987 | Hyde | 604/22 |
| 4,689,040 | 8/1987 | Thompson | 604/22 |

FOREIGN PATENT DOCUMENTS 2450597  11/1980  France ................................ 128/757

*Primary Examiner*—C. Fred Rosenbaum
*Assistant Examiner*—kathleen A. Daley
*Attorney, Agent, or Firm*—David Silverstein

[57] ABSTRACT

This invention relates to the design and application of a goniectomy instrument for the purpose of diagnostically and therapeutically removing tissue from the anterior chamber angle of the eye and for retrieving this tissue for further examination. The surgical instrument of this invention comprises in combination: a hollow, tapered shaft having a cutting edge at one end as an integral part thereof; a retractable stylet contained within the hollow interior of the tapered shaft; and an irrigation port running along the outside of the tapered shaft. This instrument is useful for excising tissue to relieve an obstruction blocking the outflow of aqueous humor from the eye as well as for providing specimens of the excised tissue for histopathological examination.

24 Claims, 1 Drawing Sheet

SURGICAL INSTRUMENT

This is a continuation of co-pending application Ser. No. 07/070,325 filed on July 6, 1987

BACKGROUND OF THE INVENTION AND DISCUSSION OF PRIOR ART

Glaucoma is a major cause of irreversible blindness in the United States. Approximately one percent of the general population has this disease. Visual loss from glaucoma is usually due to elevated intraocular pressure which damages the optic nerve. The cause for the elevated intraocular pressure is not entirely known, but, at least in many cases, appears to be due to an increase in the resistance to the outflow of aqueous humor from the eye. Aqueous humor is a fluid which circulates within the anterior portions of the eye and provides nourishment to and removes waste products from various avascular structures in the eye such as the cornea and the lens. Aqueous humor is continuously being formed within the ciliary body epithelium and is normally continuously drained out of the eye through the trabecular meshwork and Schlemm's Canal into the venous system. It is believed that the site of resistance to the outflow of aqueous humor is in the juxtacanalicular portion of the trabecular meshwork.

Treatment of glaucoma is, therefore, usually directed at lowering the intraocular pressure and thereby preventing progressive optic nerve damage and visual field loss. If medical therapy (topical eyedrops and oral tablets) and laser therapy fail to adequately lower the intraocular pressure, then glaucoma surgery is required. There are several different types of glaucoma surgery (filtration, goniotomy, trabeculotomy, cyclodialysis, etc.), but all of them have a common purpose: that is, to bypass or eliminate any blockage and thereby restore the outflow of aqueous humor from the eye.

Goniotomy and trabeculotomy surgery involve incising the abnormal tissue which is overlying or inside the trabecular meshwork in order to allow aqueous humor to flow freely into the normal outflow system. These two procedures are most commonly used in treating childhood glaucomas, but also have limited success in adult-onset glaucomas. When these surgical procedures fail, the failure is usually due to scarring which blocks the incision in the trabecular meshwork. In an attempt to avoid this problem, a technique was developed in which an intraocular diathermy probe is used to cauterize the incision edges in an attempt to reduce or eliminate scarring. However, this technique has not been proven to be any more successful than the other surgical procedures.

In identifying the reason for open-angle glaucoma and for failure of these surgical procedures and in determining the extent of the blockage and the preferred treatment, it would be useful to extract relatively large intact samples of undamaged trabecular meshwork and scar tissue and, perhaps, the surrounding tissue for histopathologic examination. Unfortunately, existing instruments for performing this surgery do not simultaneously permit the cutting and removal of relatively large and undamaged tissue specimens. The use of separate instruments as are known in the art for cutting and excision in a delicate operation like glaucoma surgery is not a satisfactory alternative. Such a procedure may entail a plurality of surgical penetrations of the inner eye thereby increasing the dangers of trauma, injury, and infection. In some cases it may also be impossible to locate a severed segment of tissue from the inner eye when using a second instrument to retrieve it. In addition, such a two-step procedure is certain to require more time than would a one-step procedure, a particularly important factor if a plurality of tissue samples are desired.

Those surgical instruments in the prior art which are capable of both cutting and removing tissue specimens in a single operation are, in general, either not adaptable for delicate glaucoma surgery, do not remove large enough tissue samples, or else result in damage to the structure of the excised tissue. For example, the prior art includes a plethora of biopsy instruments which both cut and remove tissue. In testing for carcinomous tissue, however, only relatively small tissue samples are required, and the physical structure of the tissue is usually not important. Therefore, these instruments cannot be adapted for the excision of relatively large, undamaged segments of glaucoma scar tissue. Some of the more pertinent prior art patents in this field are discussed below, and all of these patents are specifically incorporated herein by reference.

U.S. Pat. No. 3,996,935 (Banko II) is perhaps the most representative of the prior art in this field, and of its limitations. Banko II discloses a multi-purpose instrument designed for ophthalmic surgery including removal of foreign matter, blood clots, lenses and other eye tissue. The instrument includes an internal probe having a distal end for engaging tissue or foreign matter to be removed from the interior of the eye. The internal probe comprises two coaxial shafts, each having a jaw or port at its terminal end, such that the inner shaft is slidable and rotatable with respect to the outer. In other embodiments of the Banko II device, the hollow interior of the inner coaxial shaft can be utilized as a fluid irrigation channel or as a suction canal to facilitate tissue removal.

The Banko II patent, however, requires suction to engage and remove tissue. Banko's "internal probe" or "inner jaw" has cutting edges to cut tissue against the sharp opening edges of the "outer jaw" at the end of the outer hollow shaft resulting in a scissor-like cutting action which could damage the tissue. This instrument is designed to cut tissue into small pieces for removal, not to extract a relatively large, undamaged and intact tissue segment. The shape of this instrument also makes it unsuitable for goniectomy surgery. This instrument is also relatively complex, requiring an external power source for applying suction and for continuously rotating the "internal probe." Accordingly, this instrument is not suitable for conducting goniectomy surgery.

U.S. Pat. No. 3,583,390 (Jascalevich) is an example of a typical biopsy instrument. This patent discloses a biopsy device which has generally tapered, two-sided arrowhead-shaped cutting tool with a hole near the tip of the cutting edges. The shape of this biopsy instrument makes it unworkable for goniectomy surgery because the opening that would be required to introduce the instrument into the eye would be too large. Also, the large exposed surface area of the blades could cause trauma or injury to adjacent intraocular tissue during the surgical procedure. With the instrument of this patent, the tissue specimen is cut and separated from adjacent tissue by two blades — the biopsy blade and the scalpel blade — operating in a scissor-like fashion. Use of the Jascalevich instrument in the eye would necessitate making three entry wounds, one for the biopsy device and two for the scalpel blade (one for each groove). Because the two blades must be separately manipulated to excise a tissue specimen, unless a high degree of care and skill is exercised by the surgeon severe injury to the surrounding eye tissue could result. Upon withdrawing the biopsy instrument from the eye, the sharp corners of the arrowhead-like blade could catch on and injure eye tissue surrounding the entry incision. Accordingly, this instrument is also not suitable for goniectomy surgery.

U.S. Pat. Nos. 3,844,272 (Banko I); 3,929,123 (Jamshidi); and 3,007,471 (McClure) disclose surgical instruments which utilize tapered and pointed distal cutting tips in combination with coaxial members such that a sheath can slidably expose or cover the cutting tip. McClure discloses the use of an internal stylet (reference numeral 40) inside the sliding coaxial members. Other patents which show surgical sampling instruments having slidable, coaxial members, internal stylets or both include U.S. Pat. Nos. 4,308,875 (Young); 2,850,007 (Lingley); 3,893,445 (Hofsess); and 4,282,884 (Boebel).

In addition, there are a number of recent patents which are specifically directed to instruments for ophthalmic surgery. These patents include U.S. Pat. Nos. 4,590,935 (Ranalli); 4,577,629 (Martinez); 4,538,611 (Kelman); 4,570,632 (Woods); 4,041,947 (Weiss); and 4,320,761 (Haddad). These patents include discussion of such issues as the importance of irrigation during eye surgery and similar matters which have special relevance for ophthalmic surgery. None of these various instruments is suitable, however, both as a surgical tool and as a device for excising relatively large, undamaged tissue segments.

OBJECTS OF THE INVENTION

A principal object of this invention is to provide a surgical instrument for use in glaucoma surgery.

A further object of this invention is to provide a surgical instrument suitable for both cutting and extracting relatively large, intact segments of internal eye tissue.

Still a further object of this invention is to provide an instrument specially designed for goniectomy surgery comprising in combination a hollow, tapered shaft having a cutting edge at one end as an integral part thereof; a retractable stylet contained within the hollow interior of the tapered shaft; and an irrigation port running along the outside of the tapered shaft.

Specifically, it is an object of this invention to provide a surgical instrument for use in glaucoma surgery to excise a piece of tissue from the anterior chamber angle (trabecular meshwork and the inner wall of Schlemm's Canal) to therapeutically relieve the obstruction of the outflow of aqueous humor from the eye and to provide specimens of the abnormal tissues excised for histopathological examination.

These and other objects and advantages of this invention will become apparent in the following description.

DETAILED DESCRIPTION AND PREFERRED EMBODIMENTS

Figure 1:
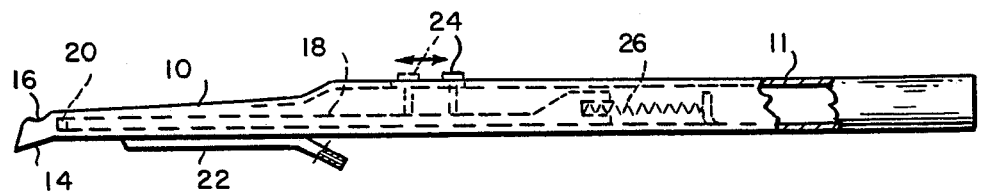
FIG. 1 is a schematic side view of the surgical instrument of this invention.
Figure 2:
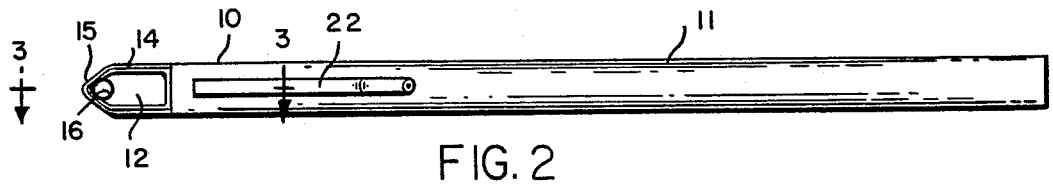
FIG. 2 is a schematic bottom view of the surgical instrument of this invention.

Referring to FIGS. 1 and 2, in the preferred embodiment the surgical instrument of this invention comprises a more or less cylindrical hollow shaft 10 which is tapered from a larger diameter at the handle end 11 to a smaller diameter at the forward cutting edge end. The tapered shaft ranges from about 0.5 to 2 mm. in diameter, being widest near the handle 11. The length of shaft 10 is about 30 mm. and the overall length of the instrument is about 120 mm. The diameter of the handle 11 is about 5 to 7 mm.

Although in the preferred embodiment shaft 10 is generally cylindrical, the shaft may have a vertical cross-section shape which ranges from circular to oval to a square or trapezoidal shape with rounded corners. The taper of shaft 10 is relatively small of approximately 5 to 15 degrees and is intended to prevent or reduce the leakage of aqueous humor around the paracentesis site. The taper is not an essential element of this invention, however; and, the use of shafts which are not tapered is within the scope of this invention.

The forward end of shaft 10 comprises a parabolic, bowl-like cavity 12 having a sharpened rim which creates a single, more or less U-shaped cutting edge 14 integral with the sides of shaft 10. The cutting edge is approximately 2.0 mm. in length and about 0.3 to 0.4 mm. in width. The distal end 15 of cutting edge 14 protrudes a distance of about 0.5 to 1.0 mm. for ease of tissue penetration and cutting. The cutting edge is softly rounded at its distal end and is generally parabolic in shape in order to avoid damage to the outer wall of Schlemm's Canal.

Figure 3:
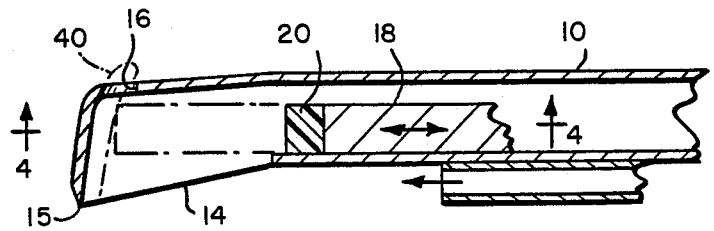
FIG. 3 is an enlarged, sectional side view of the forward end of the surgical instrument of FIGS. 1 and 2 along the axis 3—3 in FIG. 2.
Figure 4:
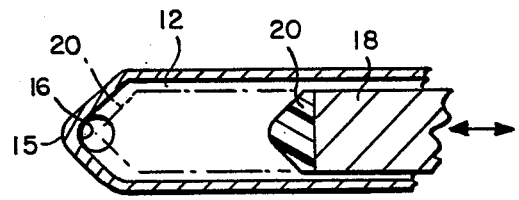
FIG. 4 is a sectional bottom view of the forward end of the surgical instrument along the axis 4—4 in FIG. 3.

In the preferred embodiment, as better shown in FIG. 3, the plane of the tip of cutting edge 14 will be at an acute angle of about 5 to 45 degrees with respect to the plane of shaft 10. The angle of cutting edge 14, however, may vary from as little as 0 degrees to greater than 45 degrees depending on surgical requirements. As shown in FIGS. 2 and 4, in the preferred embodiment the bottom of cavity 12 also includes a hole or aperture 16.

The surgical instrument of this invention also includes a retractable rod or stylet 18 located inside shaft 10. The forward end or tip 20 of stylet 18 is preferably made of a relatively soft, non-toxic material such as plastic, silicone or rubber to prevent injury or trauma to a tissue sample. The remainder of stylet 18, and all of shaft 10, can be made of any durable and corrosion-resistant metal such as stainless steel. In another embodiment, both shaft 10 and stylet 18 can be made from plastic, while cutting edge 14 is made from metal and attached to the end of shaft 10 by suitable means. There is also a lever 24 located on the handle 11 of the instrument which can manually advance and retract the stylet. There may also be a lubricated spring operated system 26 to facilitate sliding the stylet back and forth smoothly with minimal friction and force.

The surgical instrument of this invention further includes an irrigation port 22 which runs along the outside of shaft 10 on the same side of shaft 10 as cutting edge 14. The function of this irrigation port is to maintain fluid levels in the anterior chamber of the eye during a surgical procedure and to help protect the cornea and the lens from injury. The irrigation port is comprised of flexible irrigation tubing composed of plastic, silastic or similar material; and, such irrigation ports are readily commercially available.

The end of irrigation port 22 is about 3 to 5 mm. from the beginning of cutting edge 14. The diameter of the irrigation port is about 0.25 mm. or 30 gauge. The irrigation port is connected to flexible tubing (not shown) near the handle 11 of the instrument, which tubing is connected in turn to an irrigation bottle (not shown) containing sterile balanced salt solution which is suspended in the air by an adjustable intravenous stand. The rate of flow of the irrigation fluid can be adjusted by changing the height of the irrigating bottle, i.e. the higher the bottle, the faster the flow. The irrigation port has a secondary function of preventing cutting edge 14 from getting caught at the paracentesis site when the instrument is withdrawn from the eye at the end of the procedure. In some applications the instrument of this invention may be used without the irrigation port or the irrigation port 22 may be incorporated within the shaft 10 of the instrument.

FIG. 3 is an enlarged sectional side view of the cutting edge end of the surgical instrument shown in FIGS. 1 and 2 along the axis 3—3 in FIG. 2. FIG. 3 shows stylet 18 with its soft tip 20 located inside shaft 10. FIG. 3 also shows the angle of cutting edge 14 with respect to shaft 10, and the location of irrigation port 22 proximate to the cutting edge. FIG. 3 further shows in dotted lines a segment of excised tissue 40 protrucing through aperture 16 and held there in place by tip 20 of stylet 18 when stylet 18 is advanced to its forward position, all as hereinafter described.

FIG. 4 is a sectional bottom view of the cutting edge end of the surgical instrument along the axis 4—4 in FIG. 3. FIG. 4 shows the generally parabolic shape of cutting edge 14, including the softly rounded distal end 15. FIG. 4 also clearly shows aperture 16 in the bottom of cavity 12. Tip 20 of stylet 18 is preferably of a parabolic shape, as shown, in order to better fit into distal end 15 of cutting edge 14 when stylet 18 is advanced to its forward position (dotted configuration in FIG. 3).

Figure 5:
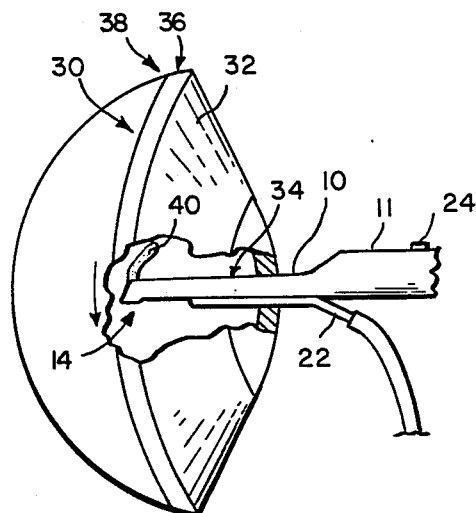
FIG. 5 is a schematic side view of an eyeball with the surgical instrument of this invention in place and ready to begin cutting and removing a tissue segment from the trabecular meshwork.

The application of the instrument of this invention to goniectomy surgery will be described by reference to FIG. 5. FIG. 5 is a schematic side view of an eyeball showing the cornea 30, the iris 32, the anterior chamber 34, the trabecular meshwork 36 which rings the iris, and Schwalbe's line 38.

The purpose of this instrument is to surgically remove a tissue segment 40 from the anterior chamber angle of the eye and to retrieve this tissue for further examination after the surgical procedure. The surgical technique is as follows:

(1) The patient is placed in the supine position on the operating table. General or local anesthesia is given.

(2) The patient' head is rotated slightly away from the side of the surgery and the eye being operated on is slightly abducted. The eye's position is fixed by locking forceps which are being held by the surgical assistant.

(3) A surgical goniolens is placed over the cornea and the air bubbles under the lens are removed with saline solution. The goniolens is positioned to leave 2 to 3 mm. of limbal cornea exposed for the incision and instrument entry. The anterior chamber angle is visualized through the goniolens under magnification with an operating microscope or a binocular head loupe.

(4) A paracentesis incision is made into the anterior chamber with a sharp knife through clear cornea about 1 mm. anterior to the limbus. The length of the incision should be about 2 to 3 mm. and parallel to the limbus.

(5) The goniectomy instrument of this invention is carefully introduced into the anterior chamber through the paracentesis site under constant irrigation. The cutting edge is passed across the center of the anterior chamber to a point in the anterior chamber angle 180 degrees from the entry site. The tapered shaft maintains a water tight seal and the irrigation maintains the anterior chamber fluid level.

(6) The cutting edge 14 is used to excise the angle tissue 40 for approximately one-third of the angle circumference. The excised tissue will be guided toward and through aperture 16 in cavity 12 (see FIG. 3) as cutting edge 14 is advanced. This will help to hold the excised tissue in place during removal. The paracentesis entry site is used as a pivotal point for the instrument as it swings across the anterior chamber.

(7) After the desired strip of angle tissue 40 is excised, the stylet 18 (not seen in FIG. 5) is advanced so that stylet tip 20 holds tissue 40 firmly against the interior of cavity 12 (see FIG. 3). Then the instrument is carefully withdrawn from the anterior chamber. The anterior chamber may then be deepened with balanced salt solution, air, or a viscoelastic substance. The paracentesis wound may also be closed with 10-0 nylon suture if necessary.

Alternatively, if desired, the instrument may be reinserted into the eye through the existing incision or through a second incision to excise and collect additional tissue samples.

Figure 6:
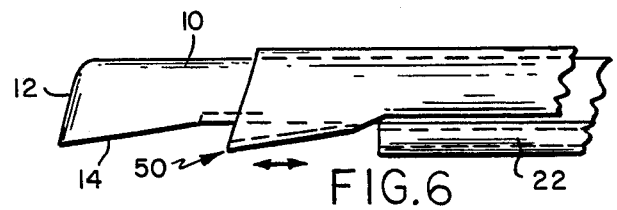
FIG. 6 is a schematic side view of an alternative embodiment of the surgical instrument of this invention showing a slidable sleeve in the open position.
Figure 7:
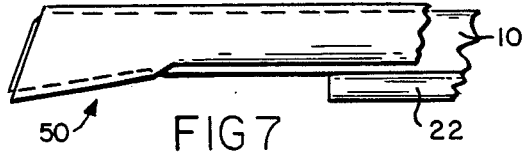
FIG. 7 is a schematic side view of the alternative embodiment of the surgical instrument of this invention with the slidable sleeve in the closed position.
Figure 8:
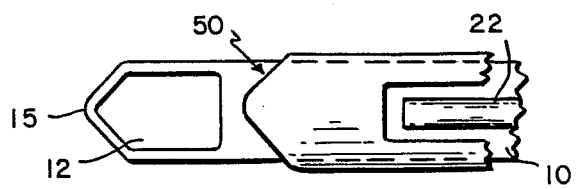
FIG. 8 is a schematic bottom view of the forward end of the instrument as shown in FIG. 6.

A modified version of the goniectomy instrument of this invention is illustrated in FIGS. 6, 7, and 8. In the modified version of the instrument, stylet 18 and aperture 16 have been eliminated, and slidable sleeve 50 capable of enclosing the distal end 15 of shaft 10 has been added. As shown in FIG. 8, the forward end of sleeve 50 is also of a generally parabolic shape in order to achieve a good fit over distal end 15.

With the modified instrument as shown in FIGS. 6, 7 and 8, the excised tissue specimen does not pass through aperture 16 to the other side of cavity 12. Instead, the tissue specimen is now directed by the interior shape of cavity 12 into hollow shaft 10. Metal sleeve 50 around distal end 15 of the shaft helps to hold the specimen in cavity 12. The metal sleeve is able to move along the length of the shaft and is controlled by a lever (comparable to lever 24 as shown in FIG. 1) located on the handle of the instrument. After the tissue specimen 40 is cut and directed up the hollow shaft 10 of the instrument, sleeve 50 is advanced to the distal end 15 of the instrument to cover cutting edge 14 and to thereby contain the tissue specimen in cavity 12 and in the hollow shaft. After the instrument is removed from the eye, the sleeve can be retracted to expose the cutting tip so that the tissue specimen can be retrieved. The sleeve also serves a secondary purpose by covering the cutting edge to protect it from inadvertently damaging other structures within the eye and to protect the cutting edge from traumatic blunting.

Many other variations and modifications of my basic design will be readily apparent to those skilled in the art. All such variations and modifications are within the spirit and the scope of this invention and, therefore, are intended to be encompassed by the following claims:

Having described my invention, what I claim is:

1. A surgical instrument designed for cutting and removing intact an elongated strip of internal tissue greater in length than the width of the instrument cutting edge, said instrument comprising:
   (a) a hollow shaft with rounded sides having a central, longitudinal axis, a handle at the rear end thereof and, at the forward end, a generally parabolic-shaped cavity which forms a bowl;
   (b) said bowl having closed sides, a closed forward wall, a closed bottom, and an open mouth such that the sides, forward wall and bottom form a continuous inner wall integral with the adjacent sides of said hollow shaft except for an opening in said bowl which communicates with the interior of said hollow shaft; and,
   (c) further wherein said open mouth is defined by a generally U-shaped rim integral with the adjacent sides of said hollow shaft and said rim is sharpened so as to form a cutting blade having side cutting edges and a distal tip.

2. The surgical instrument of claim 1 wherein said hollow shaft is tapered from a larger diameter at said handle end to a smaller diameter at said cutting edge end.

3. The surgical instrument of claim 1 wherein the distal tip of said cutting blade is rounded.

4. The surgical instrument of claim 1 further including an irrigation port along the outside of said hollow shaft.

5. The surgical instrument of claim 1 further including tissue securing and removal for securing and removing intact and elongated strip of internal tissue.

6. The surgical instrument of claim 5 wherein said tissue securing and removal means comprises a stylet slidably positioned inside said hollow shaft.

7. The surgical instrument of claim 6 wherein said stylet has a soft blunt tip at the forward end thereof designed to engage without cutting a strip of tissue between said soft tip and the inner wall of said bowl.

8. The surgical instrument of claim 6 further including lever and spring means for moving said stylet inside said shaft.

9. The surgical instrument of claim 6 further including an aperture located in the bottom of said bowl.

10. The surgical instrument of claim 5 wherein said tissue securing and removal means comprises a sleeve slidably positioned along the outside of said hollow shaft.

11. The surgical instrument of claim 10 further including lever means for moving said sleeve.

12. The surgical instrument of claim 1 wherein the mouth of said bowl is outwardly sloping with respect to the adjacent sides of said hollow shaft at an acute angle to the central longitudinal axis of said shaft.

13. A surgical instrument of comprising: a tubular member having a central, longitudinal axis and a forwardly extending leading end having an open mouth, said open mouth being outwardly sloping at an acute angle with respect to the central, longitudinal axis of said tubular member and having sharpened cutting edges; and, holding means slidably positioned within said tubular member, said holding means having a blunt front end for contacting and fixing without cutting an excised tissue segment within said tubular member.

14. The surgical instrument of claim 13 wherein said open mouth comprises a continuous cutting edge.

15. The surgical instrument of claim 13 wherein said leading end has an aperture.

16. The surgical instrument of claim 13 wherein said tubular member is forwardly tapered toward said leading end.

17. The surgical instrument of claim 13 further including an irrigation port attached to said tubular member.

18. In a surgical instrument designed for goniectomy surgery, the improvements which comprise: a hollow shaft having a handle at one end thereof and a parabolic cavity at the other end, said cavity having a sharpened rim which forms a U-shaped cutting edge integral with the sides of said shaft; a soft-tipped stylet slidably positioned inside said hollow shaft; and an irrigation port along the outside of said hollow shaft proximate to said cutting edge.

19. A method for performing goniectomy surgery on an eye and for retrieving an elongated excised tissue segment comprising the following steps: p1 (a) introducing into the anterior chamber of the eye through an incision a surgical instrument comprising a hollow shaft with rounded sides and a parabolic cavity at the forward end thereof, said cavity having sides and a bottom integral with the sides of said hollow shaft, and an open mouth having a sharpened rim which defines a generally U-shaped cutting edge, and an aperture in the bottom of said cavity, and a blunt-tipped stylet slidably positioned inside said hollow said shaft;
   (b) excising an elongated tissue segment by drawing said cutting edge along the trabecular meshwork such that the end of the tissue segment is directed through said aperture in said cavity;
   (c) advancing said stylet such that the blunt tip engages said tissue segment and holds it securely against the inside of including tissue securing and removal means for securing and removing intact an elongated strip of internal tissue.

20. The method of claim 19 further comprising he step of irrigating the anterior chamber of the eye during the surgical procedure with a sterile balanced salt solution which is introduced into the eye through an irrigation port along the outside of said hollow shaft.

21. The method of claim 19 further comprising the step of irrigating the anterior chamber of the eye during the surgical procedure with a sterile balanced salt solution which is introduced into the eye through an irrigation port located inside said hollow shaft.

22. A method for performing goniectomy surgery on an eye and for retrieving an elongated excised tissue segment comprising the following steps:
   (a) introducing into the anterior chamber of the eye through an incision a surgical instrument comprising: a hollow shaft with rounded sides having a central, longitudinal axis, a handle at the rear end thereof and, at the forward end, a generally parabolic-shaped cavity which forms a bowl; said bowl having closed sides, a closed forward wall, a closed bottom, and an open mouth such that the sides, forward wall and bottom form a continuous inner wall integral with the adjacent sides of said hollow shaft except for an opening in said bowl which communicates with the interior of said hollow shaft; further wherein said open mouth is defined by a generally U-shaped rim integral with the adjacent sides of said hollow shaft and said rim is sharpened so as to form a cutting blade having side cutting edges and a distal tip; and further including a sleeve slidably positioned along the outside of said hollow shaft;

(b) excising an elongated tissue segment by drawing said cutting edge along a trabecular meshwork such that the end of the tissue segment is directed into the parabolic cavity and up the hollow shaft;

(c) advancing said sleeve along the hollow shaft so as to enclose the parabolic cavity and the tissue segment contained therein; and, (d) removing said surgical instrument from the eye together with said elongated tissue segment intact.

23. The method of claim 22 further comprising the step of irrigating the anterior chamber of the eye during the surgical procedure with a sterile balanced salt solution which is introduced into the eye through an irrigation port along the outside of said hollow shaft.

24. The method of claim 22 further comprising the step of irrigating the anterior chamber of the eye during the surgical procedure with a sterile balanced salt solution which is introduced into the eye through an irrigation port located inside said hollow shaft.

* * * * *

UNITED STATES PATENT AND TRADEMARK OFFICE
CERTIFICATE OF CORRECTION

PATENT NO. : 4,900,300

DATED : Feb. 13, 1990

INVENTOR(S) : David A. Lee

It is certified that error appears in the above—identified patent and that said Letters Patent is hereby corrected as shown below:

Col. 6, line 1- "patient'" should be -- patient's --

Claim 5, col. 7, line 47 - after "removal" insert
-- means --
    col. 7, line 48 - "and" should be -- an --

Claim 13, col. 8, line 3 - delete the word "of"

Claim 19, col. 8, line 34 - delete "pl"; also, "(a)...."
should begin a new subparagraph
    col. 8, line 43 - "hollow said shaft" should be
-- hollow shaft --

UNITED STATES PATENT AND TRADEMARK OFFICE
CERTIFICATE OF CORRECTION

Page 2 of 2

PATENT NO. : 4,900,300
DATED : Feb. 13, 1990
INVENTOR(S) : David A. Lee

It is certified that error appears in the above-identified patent and that said Letters Patent is hereby corrected as shown below:

```
col. 8, lines 50-52 - delete "including tissue
      ...internal tissue." and insert therefor
      -- said cavity; and
          (d) removing said surgical instrument
      from the eye together with said elongated
      tissue segment intact. --
```

Claim 20, col. 8, line 53 - the word "he" should be -- the --

Signed and Sealed this

Tenth Day of September, 1991

*Attest:*

HARRY F. MANBECK, JR.

*Attesting Officer*  *Commissioner of Patents and Trademarks*